US009301806B2

(12) United States Patent
Esposito

(10) Patent No.: US 9,301,806 B2
(45) Date of Patent: Apr. 5, 2016

(54) METHODS AND PATTERNS FOR INCREASING AMPLITUDE OF ACCOMMODATIONS IN A HUMAN LENS

(71) Applicant: NUSITE TECHNOLOGIES LLC, Woodmere, OH (US)

(72) Inventor: Andrew A. Esposito, Woodmere, OH (US)

(73) Assignee: NUSITE TECHNOLOGIES LLC, Woodmere, OH (US)

( * ) Notice: Subject to any disclaimer, the term of this patent is extended or adjusted under 35 U.S.C. 154(b) by 530 days.

(21) Appl. No.: 13/653,676

(22) Filed: Oct. 17, 2012

(65) Prior Publication Data

US 2013/0103013 A1 Apr. 25, 2013

Related U.S. Application Data

(60) Provisional application No. 61/549,783, filed on Oct. 21, 2011.

(51) Int. Cl.
*A61B 18/20* (2006.01)
*A61F 9/008* (2006.01)

(52) U.S. Cl.
CPC ............ *A61B 18/20* (2013.01); *A61F 9/00812* (2013.01); *A61F 9/00838* (2013.01); *A61F 2009/0087* (2013.01); *A61F 2009/00895* (2013.01)

(58) Field of Classification Search
CPC ........... A61F 9/008; A61F 2009/00872; A61F 9/00804; A61F 9/0087
USPC ........................................................ 606/4–6
See application file for complete search history.

(56) References Cited

U.S. PATENT DOCUMENTS

| 4,724,522 | A | 2/1988 | Belgorod |
|---|---|---|---|
| 6,110,166 | A | 8/2000 | Juhasz |
| 6,197,018 | B1 | 3/2001 | O'Donnell, Jr. |
| 6,635,051 | B1 | 10/2003 | Hohla |
| 6,824,540 | B1 | 11/2004 | Lin |
| 7,101,364 | B2 | 9/2006 | Bille |
| 7,189,224 | B2 | 3/2007 | Kurtz et al. |
| 7,621,637 | B2 | 11/2009 | Rathjen et al. |
| 7,655,002 | B2 | 2/2010 | Myers |
| 2004/0049186 | A1 | 3/2004 | Hood et al. |
| 2004/0054359 | A1 | 3/2004 | Ruiz et al. |
| 2005/0107775 | A1 | 5/2005 | Huang et al. |
| 2005/0165387 | A1 | 7/2005 | Lubatschowski et al. |

(Continued)

FOREIGN PATENT DOCUMENTS

WO 2007084694 A2 7/2007

OTHER PUBLICATIONS

Novel Approaches to Correction of Presbyopia with Laser Modification of the Crystalline Lens, Myers et al., J. Refract. Surg. 14(2), 136-139 (1989).

(Continued)

*Primary Examiner* — Aaron Roane
(74) *Attorney, Agent, or Firm* — Hudak, Shunk & Farine Co. LPA

(57) ABSTRACT

A method of treating a human eye, generally to correct vision, and preferably in one embodiment to increase the amplitude of accommodation of the lens. The method utilizes a laser to create a desired pattern within the lens. Various patterns for treating the eye lens are also disclosed.

10 Claims, 4 Drawing Sheets

(56) References Cited

U.S. PATENT DOCUMENTS

| | | |
|---|---|---|
| 2007/0173795 A1 | 7/2007 | Frey et al. |
| 2007/0185475 A1 | 8/2007 | Frey et al. |
| 2010/0004643 A1 | 1/2010 | Frey et al. |
| 2011/0118712 A1 | 5/2011 | Lubatschowski et al. |
| 2011/0184392 A1 | 7/2011 | Culbertson et al. |

OTHER PUBLICATIONS

Femtosecond Laser Induced Flexibility Change of Human Donor Lenses, Schumacher et al. Vis. Res. 49(14), 1853-1859 (2009).

Experimental Increase in Accommodative Potential after Neodymium: Yttrium—Aluminum—Garnet Laser Photodisruption of Paired Cadaver Lenses, Krueger et al., Ophthalmology 108(11), 2122-2129 (2001).

First Safety Study of Femtosecond Laser Photodisruption in Animal Lenses: Tissue Morphology and Cataractogenesis, Krueger et al., J. Cataract Refract. Surg. 31(12), 2386-2394 (2005).

Fs-Laser Induced Elasticity Changes to Improve Presbyopic Lens Accommodation, Ripken et al., Graefe's. Arch. Clin. Exp. Ophthalmol. (2008) 246:897-906.

Femtosecond Laser Photodisruption of the Crystalline Lens for Restoring Accommodation, Mello et al. International Ophthalmology Clinics 51(2), 87-95 (2011).

METHODS AND PATTERNS FOR INCREASING AMPLITUDE OF ACCOMMODATIONS IN A HUMAN LENS

FIELD OF THE INVENTION

The present invention relates to methods of treating a human eye, generally to correct vision, and preferably in one embodiment to increase the amplitude of accommodation of the lens. The method utilizes a laser to create a desired pattern within the lens. Various patterns for treating the eye lens are also disclosed.

BACKGROUND OF THE INVENTION

Many humans have impaired vision due to various refractive states of the eye. Throughout history many different methods and devices have been proposed and used in order to correct vision, with the most common being glasses and contact lenses.

Surgical techniques have also been proposed to treat numerous conditions of the eye by modifying one of the components thereof, for example the cornea or a lens. Relatively older techniques have been concerned with placing incisions in various portions of the eye in order to provide a desired result. More recently, these older techniques have been replaced with laser-based treatment methods that modify a portion of the eye without cutting or substantially weakening the eye.

Various methods and devices for modifying the cornea of the eye are disclosed in U.S. Pat. Nos. 4,724,522, 6,110,166, 6,635,051, 7,101,364, 7,189224, 7,621,637 and U.S. Publications 2004/0054359 and 2005/0107775.

Regarding the use of lasers to correct various vision conditions, numerous devices and methods have been proposed.

U.S. Pat. No. 6,197,018 relates to presbyopia correction reportedly achieved by a tightening of the crystalline lens capsule. Applying laser energy to the pre-equatorial lens capsular membrane can reportedly increase the capsule tension without unwanted effects on the central clarity or on the refractive status of the eye. Wavelength selection, power, pulse duration, treatment spot size, placement, and pattern reportedly affect the accommodative and refractive effect.

U.S. Pat. No. 7,655,002 relates to methods for the creation of microspheres to treat the clear, intact crystalline lens of the eye with energy pulses, such as from lasers, for the purpose of correcting presbyopia, other refractive errors, and for the retardation and prevention of cataracts. Microsphere formation in non-contiguous patterns or in contiguous volumes reportedly works to change the flexure, mass, or shape of the crystalline lens in order to maintain or reestablish the focus of light passing through the ocular lens onto the macular area, and to maintain or reestablish fluid transport within the ocular lens.

U.S. Publication 2005/0165387 relates to surgical lasers and their controllers as well as methods for the treatment of an eye lens, especially for the treatment of presbyopia.

U.S. Publications 2007/0173795, 2007/0185475, 2010/0004643 and WO 2007/084694 relate to a system and apparatus for reportedly increasing the amplitude of accommodation and/or changing the refractive power and/or enabling the removal of the clear or cataractous lens material of a natural crystalline lens. Generally, the system comprises a laser, optics for delivering the laser beam, and a control system for delivering the laser beam to the lens in a particular pattern. There is further provided apparatus for determining the shape and position of the lens with respect to the laser. There is yet further provided a method and system for delivering a laser beam in the lens of the eye in a predetermined shot pattern.

U.S. Publication 2011/0118712 relates to an ophthalmologic laser system comprising an ultra-short pulse laser for outputting ultra-short laser pulses, focusing optics for producing at least one focal point on and/or in the eye lens of the patient's eye, a deflection mechanism for varying the position of the focal point on and/or in the eye lens, and comprising a control mechanism for controlling the deflection mechanism. The laser system is characterized in that the laser pulses output by the ultra-short pulse laser and the size of the focal point fixed by the focusing optics are configured such that a fluence can be applied below or on the disruption threshold of the material of the eye lens at the focal point wherein said fluence is at the same time sufficiently high to reportedly cause changes in at least one material property of the material of the eye lens. The laser system is also characterized in that the deflection unit can be reportedly actuated by means of the control mechanism in such a way that the focal points of a group of laser pulses are arranged such that a diffractive optical structure can be produced by the changes in the material property in the eye lens caused by way of application of the laser pulses. The invention also relates to a method for generating control data for actuating a deflection unit of such a laser system.

U.S. Publication 2011/0184392 relates to a method of treating a lens of a patient's eye that includes generating a light beam, deflecting the light beam using a scanner to form a treatment pattern of the light beam, delivering the treatment pattern to the lens of a patient's eye to create a plurality of cuts in the lens in the form of the treatment pattern to break the lens up into a plurality of pieces, and removing the lens pieces from the patients eye. The lens pieces can then be mechanically removed. The light beam can be used to create larger segmenting cuts into the lens, as well as smaller softening cuts that soften the lens for easier removal.

Additional methods and devices for correcting various vision conditions are set forth in Novel Approaches to Correction of Presbyopia with Laser Modification of the Crystalline Lens, Myers at al., J. Refract. Surg, 14(2), 136-139 (1998); Femtosecond Laser Induced Flexibility Change of Human Donor Lenses, Schumacher at al. Vis. Res. 49(14), 1853-1859 (2009); Experimental Increase in Accommodative Potential after Neodymium: Yttrium-Aluminum-Garnet Laser Photodisruption of Paired Cadaver Lenses, Krueger et al., Ophthalmology 108 (11), 2122-2129 (2001); First Safety Study of Femtosecond Laser Photodisruption in Animal Lenses: Tissue Morphology and Cataractogenesis, Krueger et al., J. Cataract Refract. Surg. 31(12), 2386-2394 (2005); Fs-Laser Induced Elasticity Changes to improve Presbyopic Lens Accommodation, Ripken et al., Graefe's Arch. Clin. Exp. Ophthalmol. (2008) 246:897-906; and Femtosecond Laser Photodisruption of the Crystalline Lens for Restoring Accommodation, Mello at al. International Ophthalmology Clinics 51 (2), 87-95 (2011).

In view of the above, there still remains a need to provide methods and laser ablation patterns that are used to reduce the force needed to change the three dimensional morphology of the human lens and further increase its amplitude of accommodation.

SUMMARY OF THE INVENTION

Accordingly, one object of the present invention is to provide methods of performing non-invasive modification of the lens of a human eye, preferably to increase the amplitude of accommodations in the lens utilizing a laser, preferably a femtosecond laser in one embodiment.

Still another object of the present invention is to provide methods and laser ablation patterns that can be used to reduce the force needed to change the three dimensional morphology of the lens, thereby increasing its amplitude of accommodations.

Another object of the present invention is to provide a method and ablation patterns that provide the lens with a multiple layer helix-plate complex.

A further object of the present invention is to provide a method which redistributes lens mass from the lens periphery to the anterior-posterior direction. In particular, in one embodiment the method is characterized by the step of creating concentric cylinders containing spiral-like columns in a lens in a posterior to anterior direction.

An additional object of the present invention is to provide a method which increases the degrees of freedom of movement between columns formed in the lens and the associated plates, wherein ends of the columns can be formed in a shape of a convex hemi-circle and can be articulated with the concave hemi-circle formed on the anterior and posterior plates of the lens.

A further object of the present invention is to provide a method that utilizes a laser to create incisions or ablation points or regions in the lens tissue to increase accommodation of the lens.

Yet another object of the present invention is to provide a method that utilizes laser ablation to create at least two concentric cylinders comprising columns that have a shape of a segment of a spiral that are located outside of a central visual axis of the lens in order to preserve central vision and reduce potential glare.

A further object of the present invention is to provide methods and patterns which create a spring force that counterbalances the force generated by the ciliary body and allows the lens to actively return to an emmetropic state.

Still another object of the invention is to provide methods which consider one or more of patient's age, size of the lens, and the amount of nuclear sclerotic change present and further determine the amount of accommodative amplitude needed.

An additional aspect of the invention is a method for modifying the structure of a human lens to increase amplitude of accommodation, comprising the steps of applying laser energy to a plurality of points located on a surface of or within a lens of a human eye to form at least two concentric cylinders, each cylinder comprising a plurality of columns having a longitudinal length disposed at an angle with respect to a visual axis of the lens.

An additional aspect of the invention is a method for modifying the structure of the lens of the eye, comprising the steps of applying laser energy to a lens of a human eye and forming a multiple layer helix-plate complex comprising a posterior plate and an anterior plate, wherein at least two concentric cylinders are formed in the lens between the anterior and posterior plates, and wherein each cylinder comprises a plurality of columns comprising a segment of a spiral and disposed at an angle with respect to a visual axis of the eye.

An additional aspect of the invention is a method for delivering a laser beam to a lens of an eye, comprising the steps of obtaining a laser; directing a laser beam from the laser at a first focal point at a location in the lens of the eye; and directing the laser beam at least a second focal point in the lens of the eye and creating at least two concentric cylinders each comprising columns in the lens, wherein the columns have a shape of a segment of a spiral.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

The present invention relates to methods and patterns for modifying the structure of a human eye lens, in particular utilizing a laser, to treat or correct various conditions or imperfections such as presbyopia, myopia, hyperopia, astigmatism and reduction of higher order aberrations, i.e. trefoil. Laser pulses are used to create or generate ablation points or areas, also referred to as optical breakdowns that change the three dimensional morphology of the lens and in preferred embodiments increase the amplitude of accommodation or elasticity of the lens.

Figure 1:
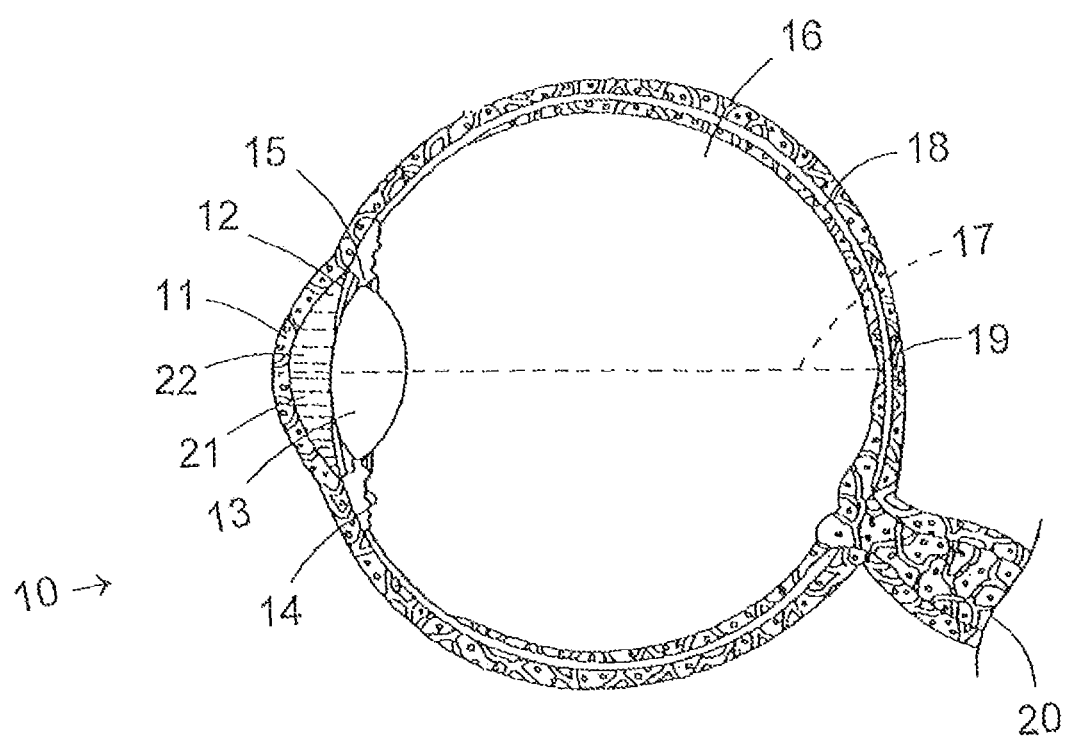
FIG. 1 illustrates a cross-sectional representation of a human eye.

FIG. 1 illustrates a cross-sectional view of a human eye. The eye 10 includes a cornea 11 which is generally a transparent layer of tissue that forms the exterior surface of the eye through which light enters the eye. The iris 12 is the readily recognizable colored portion of the eye 10 that controls the amount of light entering the eye by changing the pupil located at the center thereof. The natural lens 13 is located posterior to the iris 12. The term "lens" when utilized herein refers to the natural lens, crystalline lens or ocular lens, wherein said terms may be utilized interchangeably herein. The ciliary muscle 14 changes the shape of the lens to allow for focusing of a visual image. A neural feedback mechanism from the brain allows the ciliary muscle 14 through the attachment of the zonules 15 to change the shape of the lens.

Light generally enters the eye through the cornea 11 and pupil, further proceeds through the lens 13 through the vitreous 16 along a visual axis 17 and reaches the retina 18 at the back of the eye where an image is formed at the macula 19 that is transferred by the optic nerve 20 to the brain. Located between the cornea 11 and lens 13 is an anterior chamber 21 that is filled with a liquid generally referred to as an aqueous 22.

One current theory regarding the physiology of the lens and how it changes shape is as follows. When the ciliary muscles contract, they transmit tensile forces into the lens-capsule complex including the lens through the zonule fibers. The zonule fibers are connected at an area anterior and posterior to the periphery of the lens. When force is applied, changes in both the anterior to posterior length of the lens and lateral diameter of the lens are produced. It is through these changes, as well as a change in the central curvature of the lens that allows the lens to have a range of accommodation.

Numerous theories exist as to why accommodation is lost in the human crystalline lens. As the human lens ages, lens proteins are produced in the equatorial-peripheral region of the lens. Additionally, the composition of proteins of the lens can change, for example, there can be an increase in the concentration of water insoluble proteins. Over time, the proteins form layers that are added to the periphery of the lens, which in turn causes the prior layers of protein deposited to become more compact. Some believe that this increase in density of the lens proteins cause a resultant gradient in stiffness of the protein matrix and more force is thus required to change the lens shape. In addition, as the lens increases in diameter, the length in which the ciliary muscles can linearly move and generate force is reduced. Together, these two mechanisms are thought to be the pathophysiology behind progressive loss in amplitude of accommodation. Another theory for the development of presbyopia is the increasing sclerosis of the lens over time. Regardless of theory, there is still a need to correct the deformation ability of the lens.

The methods of the present invention comprise the step of modifying the lens of an eye utilizing a laser to form a specific ablation, cutting or incision pattern thereby resulting in minimal invasiveness, making risk of infection negligible as no exterior wound is created. The pattern created on the lens reduces the force needed to change the three dimensional morphology of the lens and thereby increases its amplitude of accommodation.

Various lasers are suitable for use in the present invention. In one embodiment a femtosecond laser is utilized to create the desired ablation pattern. Photodisruption utilizing short laser pulses has been found to offer desirable results in ophthalmic surgery. Femtosecond lasers are currently preferred over nanosecond lasers as they are believed to result in fewer side effects such as tissue breakdown, shockwaves, and stresswaves at the area of laser application. Thus, very short laser pulses such as femtosecond laser pulses provide desired precision for lens surgery. Currently in one embodiment a commercially available femtosecond laser used in conical ablation is 500 fs with a pulse energy of 1-6 µJ with a spot separation of 8-10 mm, pulse frequency is between 15-30 Khz and the wave length of light is 1050 nm. However, it is to be understood that other lasers may be utilized, having different wavelengths, power pulse duration, pulse frequency, spot separation and energy, etc.

The desired laser beam is directed through a patient's cornea and is focused on the surface of or within a patient's lens for the purpose of modifying the lens structure. The focal point of the laser beam is capable of being located at any point within the three dimensional space of the lens. Various devices are known in the art to control laser parameters, such as focal point location, energy level, pulse duration, and frequency. For example, such as available as a LenSx® system from Alcon Laboratories of Fort Worth, Tex. or a LensAR laser system from LensAR Inc. of Orlando, Fla. or Topcon Europe Medical B.V. of Rotterdam, Netherlands.

The laser beam passes through the cornea without any substantial damage to corneal tissue because the energy density of the laser within the corneal tissue is chosen to be at subthreshold levels. The threshold energy level or energy density is attained or surpassed at the focal point of the laser beam within the lens. Thus, at the focal point, in the lens, sufficient energy exists to ablate the lens. The lens tissue at the focal point is ablated or destroyed in a volume essentially located at or centered on the focal point. Stated in another manner, the laser pulse creates a laser-induced optical breakdown at the focal point. The volume of lens tissue destroyed depends upon the characteristics of the particular laser pulse incident on the lens and the characteristics of the lens tissue itself.

At the ablation or focal point, the laser beam energy breaks molecular bonds and ionizes molecules and atoms, converting the tissue from a solid to a plasma which converts to a gas. It is believed that the gas is eventually absorbed by the lens tissue.

The methods of the present invention utilize multiple ablation points to form specific patterns in order to increase amplitude of accommodation of the lens. By positioning one focal point close to another, it is possible to disrupt or ablate tissue in a three dimensional pattern. The precision of the pattern is only limited by the size of the focal point. Thus, the method utilizes the laser to create multiple ablation points, lines, or areas, for example by focusing a laser at a first location within a lens and creating an ablation point. As the procedure continues, the focal point of the laser is moved to a different location in the lens according to a desired pattern and second, third, and additional ablation points are created to form the desired pattern on the lens.

In a preferred embodiment, the laser ablation patterns utilized result in the construction of a multilayer helix-plate complex within the lens. In one embodiment, concentric cylinders comprising spiral-like or helical columns are created in a posterior to anterior direction in the lens. This results in redistributing mass from the lens periphery to the anterior and posterior region and vice versa. By starting at the posterior of the lens and working forward to the anterior surface of the lens, the prior ablation points are avoided.

In a preferred embodiment, the ablation pattern forms a plurality of cylinders on the lens, generally having a length extending in an anterior-posterior direction. The term cylinder when utilized herein refers to tube-like structures that are preferably hollow (with an unablated central visual axis of the lens located therein) and can be cylindrical or substantially cylindrical. Thus, the cylinders can be completely cylindrical or slightly or mostly flattened, oval-like, or the like. In a preferred embodiment the cylinders are curved in an anterior-posterior direction.

Figure 2A:
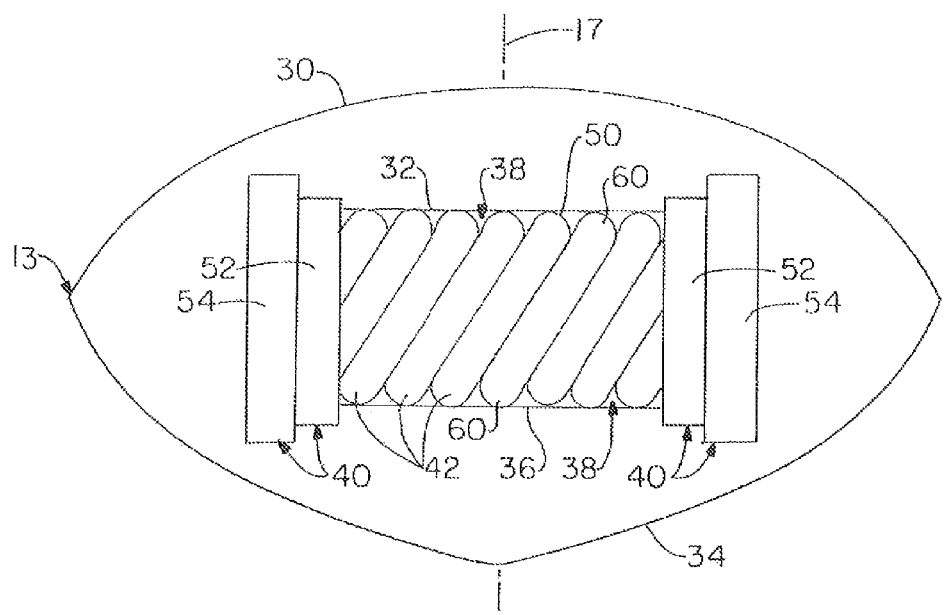
FIG. 2a is a schematic representation of a partial cross-sectional lateral view of one embodiment of an intra-lenticular ablation pattern with three cylinders, namely a first cylinder, a second cylinder, and a third cylinder, each comprising helical or angled columns with column ends that are rounded or formed as hemi-circles at the plate ends of columns, these are articulated to the anterior and posterior plates which comprise a corresponding concave depression or structure.

FIG. 2a is a schematic representation of a partial cross-sectional lateral view of one embodiment of an intra-lenticular ablation pattern with three cylinders 40, namely a first cylinder 50, a second cylinder 52, and a third cylinder 54, each comprising helical columns 42 with column ends 60 that are rounded or formed as hemi-circles on the plate ends of columns 42, these are articulated to the anterior and posterior plates 32, 36 respectively, which comprise a corresponding concave depression or plate end structure 38. The ablation pattern enhances the degree of freedom of movement between the anterior and posterior plates 32, 36 and the individual helical columns 42. The columns 42 are only shown for one section of the first cylinder 50, with the first cylinder 50 comprising repeating helical columns 42 having a longitudinal length with a 60 degree rotational confirmation relative to the visual axis 17. The cylinders are preferably centered around the visual axis and the orientations of the columns are parallel to the visual axis, with the columns central axis rotated by a variable amount relative to the visual axis. The second and third cylinders 52, 54, respectively, are shown in cross-section and also comprise similar helical columns as shown for first cylinder 50, with the helical columns oriented preferably orthogonal, i.e. 90 degrees, to the columns of the adjacent cylinder. The third cylinder includes columns 42 situated at a 60 degree rotational confirmation relative to the visual axis 17, like the columns 42 of first cylinder 50.

In FIG. 2a, the height of the second cylinder 52 measured in relation to the optical axis 17 is greater than the height of the first cylinder 50. Likewise, the height of the third cylinder 54 is greater than the height of both the second and first cylinders. Thus, in one embodiment, the height of an outer or more peripherally disposed cylinder is greater than the height of a corresponding inner cylinder, with the height measured in relation to the optical axis 17. This will cause a leaf spring-like effect with anti-centralpedal movement of the lens material, i.e. when the lens transitions from a disaccommodative state to an accommodative state.

In a further embodiment, the height of the first or an inner cylinder is greater than the height of any additional peripheral cylinders, with height measured in relation to the visual axis 17. For example, a reverse pattern to the pattern set forth in FIG. 2a is utilized, wherein the innermost cylinder has the greatest height and the outermost cylinder is the shortest. Such a pattern will cause a greater stepping of the central portion of the lens and help increase the dioptric power of the lens.

Figure 2B:
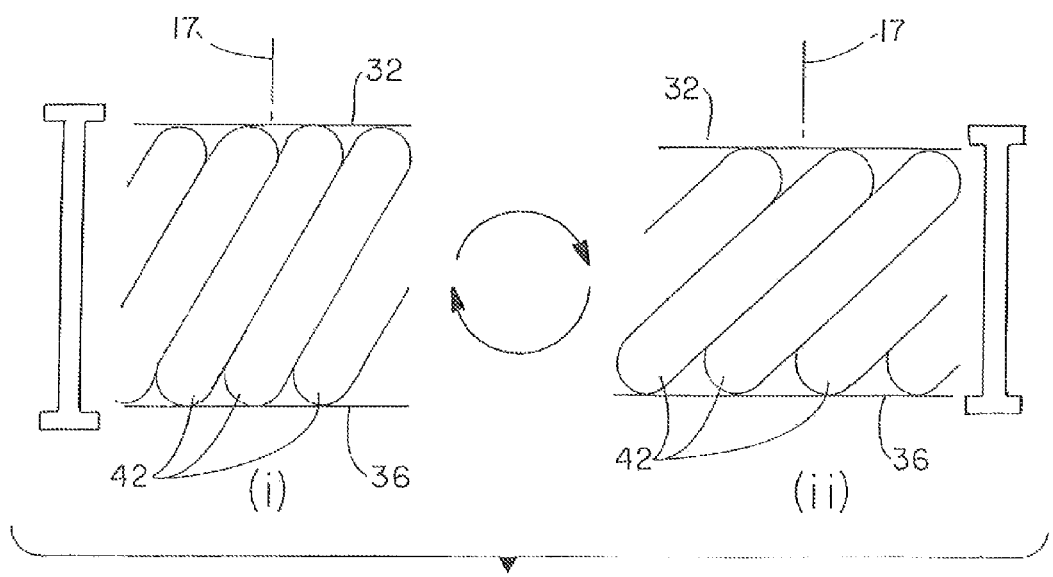
FIG. 2b is a schematic representation showing cross-sectional lateral views of i) a portion of a column having a 60 degree rotational confirmation relative to the visual axis corresponding to the lens in an accommodated state and a view showing the columns having a 30 degree rotational confirmation relative to the visual axis corresponding to the lens in a disaccommodated state.

FIG. 2b illustrates partial cross-sectional lateral views of several repeating helical columns 42 with the first view i) having a 60 degree rotational confirmation relative to the visual axis 17 with view i) corresponding to the lens in the accommodated state with the longitudinal length of the columns being positioned more parallel to the visual axis which places a greater amount of mass in line with the anterior-posterior axis. This decreases the peripheral circumference of the lens, causing the lens to conform to a more spherical structure resulting in an increase in the optical power of the lens. The second view ii) of FIG. 2b illustrates the helical column 60 having a 30 degree rotational confirmation relative to the visual axis 17 and corresponds to the lens in a disaccommodated state. In the second view ii) the height or length of the columns is more orthogonal when compared to the visual axis 17 and therefore places a greater amount of mass in line with the periphery of the lens. This relative positioning increases the peripheral circumference of the lens, causing the lens to flatten resulting in a decrease in the optical power.

Figure 3:
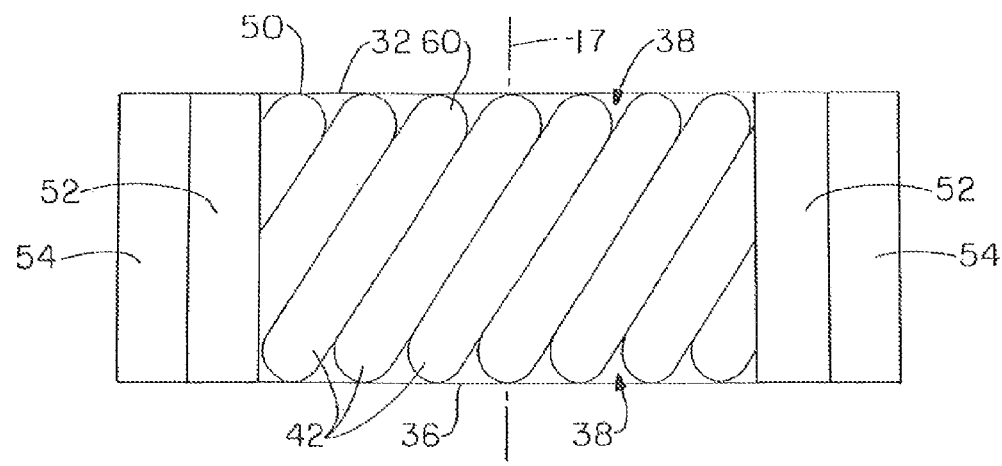
FIG. 3 is a schematic representation of an alternative embodiment of a laser ablation pattern wherein the ends of a spiral column are in the shape of a convex hemi-circle and are articulable with the concave hemi-circle on the anterior and posterior plates.

FIG. 3 illustrates an alternative ablation pattern shown in relation to anterior plate 32 and posterior plate 36 and visual axis 17. Three cylinders 50, 52, and 54 are illustrated and include helical columns 42. The column ends 60 are rounded and are substantially hemi-circles when considered in cross-section. The column ends 60 can be articulated in relation to the anterior and posterior plates 32 and 36 respectively which include a corresponding curved plate end structure 38 which can be generally referred to as a concave depression. First cylinder 50 comprises a plurality of columns 42 having a 60 degree rotational confirmation relative to the visual axis. Second and third cylinders 52 and 54 respectively, are composed of similar columns oriented in the same axis of the adjacent cylinder's columns. The pattern illustrated in FIG. 3 allows maximal movement of the plurality of cylinders in a centralpedal fashion in the accommodative state. By forming the columns in the same direction, internal friction between adjacent columns is minimized to reduce the required force transfer mass from the periphery to the anterior-posterior region of the lens.

In order to increase the degree of freedom of movement between the columns of the cylinders and associated plates, the ends of the columns in one embodiment can be formed having rounded or substantially spherical ends, for example and have the shape of a convex hemi-circle which can be articulated with a concave hemi-circle on the anterior and posterior plates, for example as illustrated in FIG. 3.

The methods of the present invention in a preferred embodiment preserve a portion of the lens material located adjacent the optical axis of the lens. By not cutting or ablating the material near the optical axis of the lens, it is believed that central vision is preserved. The potential to produce glare with the methods is also reduced or avoided. The size of the area not modified adjacent to the central optical axis can vary and range from a diameter of about 1 mm to about 7 mm, desirably from about 3 mm to about 5 mm and preferably is about 4 mm. It is to be understood that the non ablated area around the central optical axis does not have to be circular or cylindrical and can be elliptical or any other shape, for example.

Figure 4:
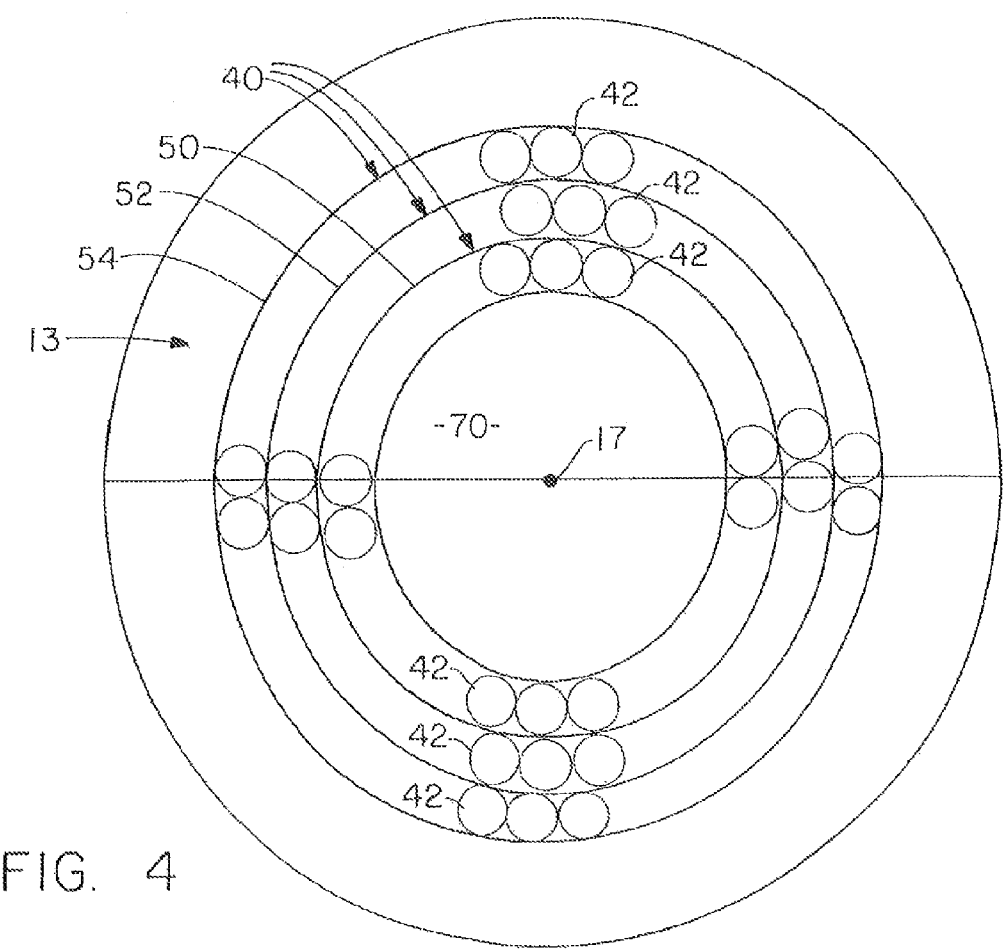
FIG. 4 is a schematic representation of an anterior-posterior view of the lens showing placement of an ablation pattern outside of a central visual axis.

FIG. 4 illustrates one embodiment of an ablation pattern of the present invention including an area not modified adjacent the central optical axis 17 of lens 13. FIG. 4 is a cross-sectional view in an anterior-posterior direction of the lens that includes an ablation pattern including three cylinders including first cylinder 50, second cylinder 52, and third cylinder 54. The cylinders are located adjacent to and in contact with a neighboring cylinder. The columns 42 of each cylinder 40 are represented by individual circles. The pattern illustrated in FIG. 4 can increase the degree of freedom of movement that the helical columns 40 may move relative to the plates. The central area 70 adjacent optical axis 17 is free from ablation and has a diameter of 4 mm as illustrated. It is additionally illustrated that each cylinder has width measured perpendicular to the optical axis of 0.5 mm. The cylinders 40 present have a maximum diameter of 7 mm in this embodiment.

The columns created have a defined angle, thickness, and total number in order to create a spring force which counterbalances the force generated by the ciliary muscles. The columns are created having a tilt angle with respect to the visual axis that allows maximal movement in either direction. That said, the tilt angle of each column measured in a longitudinal direction of a column ranges generally from about 30 degrees to about 60 degrees, and preferably is about 45 degrees with respect to the visual axis of the lens. It is noted hereinabove that the angle between columns in adjacent cylinders can vary. In some embodiments the columns in adjacent cylinders are parallel to each other. However, when the columns in adjacent cylinders are angled with respect to each other, the angle ranges generally from about 40 degrees to about 140 degrees, desirably from about 60 degrees to about 120 degrees, and preferably one column of a cylinder is located 90 degrees from a second column in a different adjacent cylinder. The thickness or width of the columns can vary and range generally from about 20 µm to about 70 µm, desirably about 35 μm to about 65 μm and preferably is about 50 μm in various embodiments. The longitudinal length of each column from a first column end to a second column end ranges generally from about 1.0 mm to about 2.5 mm, and preferably is about 2 mm. The maximum length or height of each cylinder generally depends on the tilt angle and the longitudinal length of the columns. At least two cylinders are created to form the multiple layer helix-plate complex. Generally the number of the cylinders ranges from 2 to about 6 and preferably 3 or 4. The number of columns per cylinder ranges from about 12 to about 36, desirably from about 24 to about 30, and preferably from about 26 to about 28. The width of each cylinder individually ranges generally from about 0.3 mm to about 1.0 mm, desirably from about 0.4 mm to about 0.6 mm, and preferably from about 0.5 mm to about 0.6 mm. The angle, thickness and number of cylinders allow the lens to actively return to an emmetropic state. The cylinder and column construction varies based upon factors such as patient's age, the size of the lens, and the amount of nuclear sclerotic change present, among others.

By providing a plurality of concentric cylinders comprising angled or spiral columns, several adjacent layers of lens material are formed. Each individual layer or cylinder can freely move, generally sliding, past the other layers such as cylinders or adjacent lens tissue for the purpose of redistributing mass from the midsection of the peripheral lens to the anterior and posterior regions of the lens, for example as shown in FIG. 2b. The spiral pattern formed in the lens creates a spring-like effect from the compression and/or expansion movements from the force of the ciliary muscle on the adjacent lens capsule. The force and speed of the spring-like effect derived from the cylinders comprising the spiral-like or helical column segments is dependent from on the spring constant which would be a function of the level of the nuclear sclerotic change in the presbyopic lens. Generally, the higher the grade of nuclear sclerotic change, the greater the spring constant functions would be. Additionally, for a patient having a relatively higher grade of cataract, the greater the resistance is to the deformity of the lens. Additionally, by coupling the resting state of the lens with an emmetropic refraction, a maximal accommodative amplitude can be achieved in various embodiments that is dependent upon the spring constant to help actively return the lens to its resting state position.

Figure 5A:
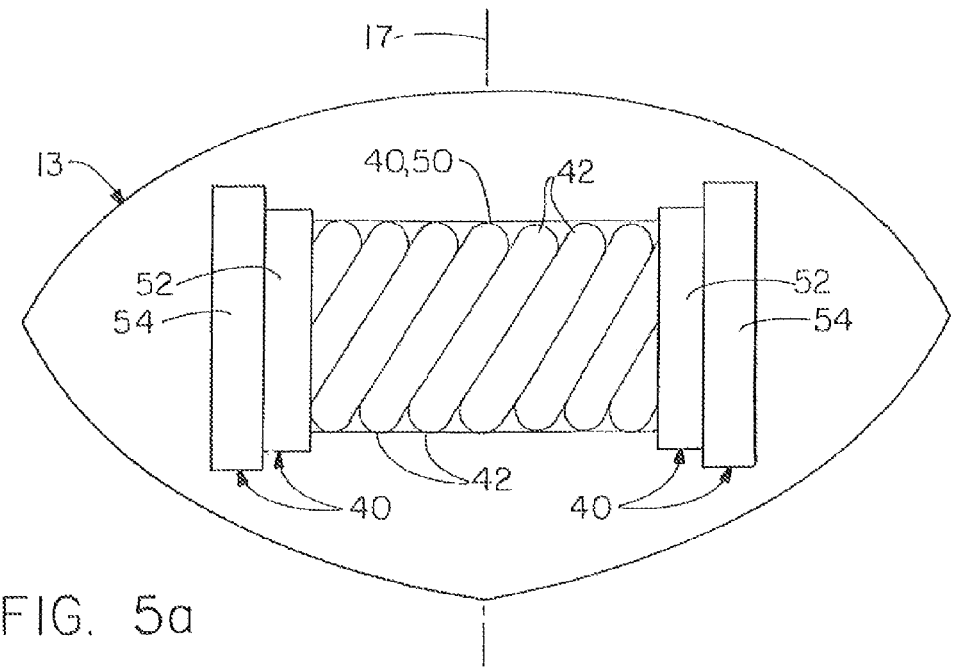
FIG. 5a is a schematic representation of a partial cross-sectional equatorial view particularly illustrating an ablation pattern wherein the inner cylinder includes columns having a 60 degree tilt with respect to the central visual axis, wherein the middle and peripheral cylinders have the same height as the inner cylinder in the relaxed disaccommodated state.

FIG. 5a illustrates an equatorial partial cross-sectional view through a lens 13 illustrating an ablation pattern wherein the first cylinder 50 includes columns 42 having a longitudinal length extending at an angle of 60 degrees in relation to central visual axis 17. Additionally, the middle or second cylinder 52 and the peripheral or third cylinder 54 have the same height measured in relation to the visual axis 17 in a relaxed disaccommodative state.

Figure 5B:
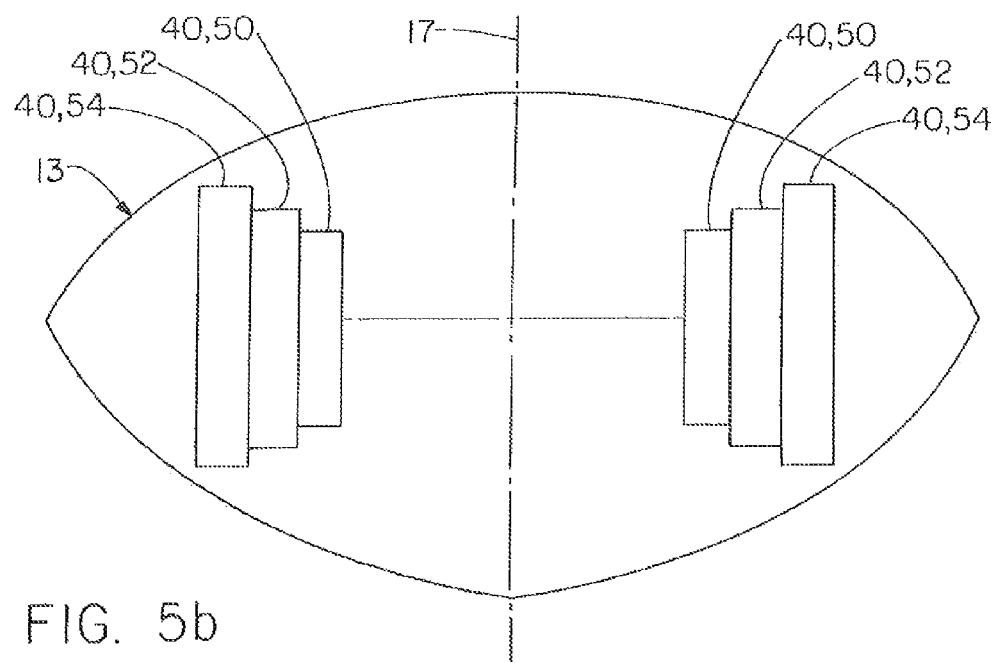
FIG. 5b is a schematic representation of a partial cross-sectional equatorial view particularly illustrating an ablation pattern having three cylinders, wherein from a direction from the inner cylinder to the outer cylinder, the cylinder height progressively increases, with the lens being shown in a relaxed disaccommodative state.

To increase the effectiveness of the force generation by the ciliary muscle conversion to mechanical movement of the lens material the outer rings or cylinders are formed having a greater height or taller than the inner rings or cylinders, see FIG. 5b. More specifically, the peripheral or third cylinder 54 is taller or has a greater height than middle or second cylinder 52, which has a greater height than the inner or first cylinder 50, measured in relation to the visual axis 17. This would create a leaf spring in the equatorial region to leverage effect of the outer rings and increase the effective shift and movement of mass from an anterior-posterior periphery to the mid-periphery which would also result in an increase in the thickness of the lens.

In view of the description set forth herein, methods and patterns for modifying the structure of the human lens in order to change the three dimensional morphology and thereby accommodation of the lens have been set forth. Modifications or variations to the subject matter of this invention may occur to those of ordinary skill in the art upon reviewing the description of this specification. Such modifications and variations within the spirit of the invention are encompassed within the scope of this specification.

While in accordance with the patent statutes, the best mode and preferred embodiment have been set forth, the scope of the invention is not limited thereto, but rather by the scope of the attached claims.

What is claimed is:

1. A system for modifying the structure of a lens to produce a modified lens having increased amplitude of accommodation, comprising:
    a laser that generates laser energy in the form of a laser beam; and
    a control system programmed to control parameters of the laser and direct the laser beam at a point on a surface of or within a three dimensional space of the lens such that a pattern is formed on the lens comprising at least two concentric cylinders, each cylinder comprising a plurality of columns having a longitudinal length disposed at an angle with respect to a central visual axis of the lens.

2. The system for producing the modified lens according to claim 1, wherein the control system directs the laser beam to produce a pattern wherein a column of a first cylinder is parallel to a column of a second cylinder.

3. The system for producing the modified lens according to claim 1, wherein the control system directs the laser beam to produce a pattern wherein an inner cylinder has either a greater or shorter longitudinal length than a peripheral cylinder.

4. The system for producing the modified lens according to claim 1, wherein the control system directs the laser beam to produce a pattern wherein the longitudinal length of the columns extend in a posterior to anterior direction of the lens, and wherein each column, individually, is situated at an angle of about 30 to about 60 degrees with respect to the visual axis, wherein from 2 to about 6 cylinders are present, and wherein a column of a first cylinder is arranged at an angle of about 40 degrees to about 140 degrees with respect to a second column in a different cylinder.

5. The system for producing the modified lens according to claim 1, wherein the control system directs the laser beam to produce a pattern wherein ends of the columns are substantially convex in shape and are articulable with a substantially concave surface on an anterior or posterior plate.

6. The system for producing the modified lens according to claim 1, wherein the control system directs the laser beam to produce a pattern wherein the plurality of columns are outside of the central visual axis, wherein each cylinder, individually, has a width that ranges from about 0.25 to about 0.5 mm, and wherein the longitudinal length of each column independently ranges from about 1 mm to about 2.5 mm.

7. The system for producing the modified lens according to claim 6, wherein the control system directs the laser beam to produce a pattern wherein the central visual axis has a diameter of about 1 mm to about 7 mm.

8. A system for modifying the structure of a lens to produce a modified lens having increased amplitude of accommodation, comprising:
    a laser that generates laser energy in the form of a laser beam; and
    a control system programmed to control parameters of the laser and direct the laser beam at a point on a surface of or within a three dimensional space of the lens such that a pattern is formed on the lens comprising a multiple layer helix-plate complex comprising a posterior plate and an anterior plate, wherein at least two concentric cylinders are present in the lens between the anterior and posterior plates, and wherein each cylinder comprises a plurality of columns comprising a segment of a spiral and disposed at an angle with respect to a visual axis of the eye.

9. The system for producing the modified lens according to claim 8, wherein the control system directs the laser beam to produce a pattern wherein each column, individually, is situated at an angle of about 30 to about 60 degrees with respect to the visual axis, and wherein from 2 to about 6 cylinders are present.

10. The system for producing the modified lens according to claim 9, wherein the control system directs the laser beam to produce a pattern wherein a column of a first cylinder is arranged at an angle of about 40 degrees to about 140 degrees with respect to a second column in a different cylinder, wherein ends of the columns are substantially convex in shape and are articulable with a substantially concave surface on an anterior or posterior plate, and wherein the central visual axis has a diameter of about 1 mm to about 7 mm.

* * * * *